United States Patent
Charra et al.

(10) Patent No.: US 10,544,276 B2
(45) Date of Patent: Jan. 28, 2020

(54) PROCESS FOR THE DEPOLYMERIZATION OF A POLYESTER COMPRISING OPAQUE POLYETHYLENE TEREPHTHALATE

(71) Applicant: IFP Energies Nouvelles, Rueil-Malmaison (FR)

(72) Inventors: Cyprien Charra, Lyons (FR); Frederic Favre, Lyons (FR); Adrien Mekki-Berrada, St Etienne (FR); Olivier Thinon, Roanne (FR)

(73) Assignee: IFP Energies Nouvelles, Rueil-Malmaison (FR)

(*) Notice: Subject to any disclaimer, the term of this patent is extended or adjusted under 35 U.S.C. 154(b) by 0 days.

(21) Appl. No.: 16/315,240

(22) PCT Filed: Jul. 4, 2017

(86) PCT No.: PCT/EP2017/066577
§ 371 (c)(1),
(2) Date: Jan. 4, 2019

(87) PCT Pub. No.: WO2018/007356
PCT Pub. Date: Jan. 11, 2018

(65) Prior Publication Data
US 2019/0161595 A1    May 30, 2019

(30) Foreign Application Priority Data
Jul. 5, 2016   (FR) .................... 16 56423

(51) Int. Cl.
C08J 11/24    (2006.01)
C07C 67/03    (2006.01)
C07C 67/56    (2006.01)

(52) U.S. Cl.
CPC ............... *C08J 11/24* (2013.01); *C07C 67/03* (2013.01); *C07C 67/56* (2013.01); *C07C 2601/16* (2017.05); *C08J 2367/02* (2013.01)

(58) Field of Classification Search
None
See application file for complete search history.

(56) References Cited

U.S. PATENT DOCUMENTS

| | | | |
|---|---|---|---|
| 3,907,868 A | 9/1975 | Currie et al. | |
| 6,645,445 B1 | 11/2003 | Inada et al. | |
| 2004/0147624 A1* | 7/2004 | Inada | C07C 67/56 521/48 |
| 2016/0060419 A1* | 3/2016 | Allen | C07C 51/09 521/48.5 |

FOREIGN PATENT DOCUMENTS

| | | |
|---|---|---|
| EP | 1130011 A1 | 9/2001 |
| WO | 2016/096767 A1 | 6/2016 |

OTHER PUBLICATIONS

International Search Report dated Aug. 10, 2017 issued in corresponding PCT/EP2017/066577 application (2 pages).

\* cited by examiner

*Primary Examiner* — Clinton A Brooks
*Assistant Examiner* — Kofi Adzamli
(74) *Attorney, Agent, or Firm* — Millen, White, Zelano and Branigan, P.C.

(57) ABSTRACT

A subject-matter of the invention is a process for the depolymerization of a polyester feedstock comprising opaque PET, the said process comprising at least the stages of conditioning, of depolymerization and of separation of the diol and of separation of the liquid effluent rich in monomers, followed by a decolouration stage.

15 Claims, No Drawings

PROCESS FOR THE DEPOLYMERIZATION OF A POLYESTER COMPRISING OPAQUE POLYETHYLENE TEREPHTHALATE

TECHNICAL FIELD OF THE INVENTION

The invention relates to a process for the depolymerization of a polyester, in particular the terephthalate polyester, for the purpose of recycling it in a polymerization unit.

PRIOR ART

The chemical recycling of polyethylene terephthalate (PET) has formed the subject of numerous research studies targeted at breaking down the PET recovered in the form of waste into monomers which will again be able to be used as feedstock for a polymerization process.

Numerous polyesters are produced by circuits for collecting and sorting materials. In particular, the PET can originate from the collecting of bottles, containers, films, resins and/or fibres consisting of PET. The polyester resulting from collecting and recycling industries is known as recycled polyester.

Recycled PET can be classified into four main categories:
- clear PET, predominately composed of uncoloured transparent PET (generally at least 60% by weight) and azure coloured PET, which does not contain pigments and can be sent to mechanical recycling processes,
- dark or coloured (green, red, and the like) PET, which can generally contain up to 0.1% by weight of dyes or pigments but remains transparent or translucent,
- opaque PET, which contains a significant amount of pigments at contents typically varying between 0.25% and 5% by weight, which pigments are used to opacify the polymer, and which is ever increasingly used, for example in the manufacture of food containers, such as milk bottles, in the composition of cosmetic, plant-protection or dye bottles,
- multilayer PET, which comprises layers of plastics other than PET or a layer of recycled PET between layers of virgin PET, that is to say a PET which has not been subjected to recycling, or a film of aluminium, for example. This PET is used, after thermoforming, to produce packagings, such as containers.

The collecting industries which make it possible to supply the recycling industries are structured differently depending on the country. They are changing so as to maximize the amount of plastic recovered in value from the waste as a function of the nature and of the amount of the streams and of the sorting technologies.

The industry for recycling these different streams generally consists of a first stage of conditioning in the flake form in which bales of raw packaging are washed, purified and sorted, ground and then again purified and sorted to produce a stream of flakes generally containing less than 2% of impurities (glass, metals, other plastics, wood, paper, board, inorganic elements), preferably less than 1% of impurities.

Clear PET flakes can subsequently be subjected to an extrusion-filtration stage which makes it possible to produce extrudates which can subsequently be reused as a mixture with virgin PET to produce new products (bottles, fibres, films). A stage of solid state polymerization under vacuum (known under the acronym SSP) is necessary for food uses. This type of recycling is known as mechanical recycling.

Dark or coloured PET flakes can also be recycled mechanically. However, the colouration of the extrudates formed from the coloured streams limits the uses and this PET is generally used to produce packaging strips or fibres. The outlets are thus more limited.

The presence of opaque PET containing high contents of pigments presents problems to recyclers as opaque PET detrimentally affects the mechanical properties of recycled PET. Opaque PT is currently collected with coloured PT and is found in the coloured PET stream. In view of the development of uses for opaque PET, contents of opaque PET in the coloured PET stream are currently between 5% and 10% and are increasing. In a few years time, it will be possible to achieve contents of opaque PET in the coloured PET stream of greater than 20%. In point of fact, it has been shown that, above 10-15% of opaque PET in the coloured PET streams, the mechanical properties of the recycled PET are detrimentally affected and prevent recycling in the form of fibres, the main outlet of the industry for coloured PET.

The main pigments used are metal oxides, such as $TiO_2$, $CoAl_2O_4$ or $Fe_2O_3$, silicates, polysulfides and carbon black. The pigments are particles with a size generally of between 0.1 and 10 μm and predominantly between 0.4 and 0.8 μm. The complete removal of these pigments by filtration, which is necessary in order to envisage recycling the opaque PET, is technically difficult. This is because, on the one hand, these particles are highly blocking and, on the other hand, some pigments are known to catalyse the polymerization reaction of PET under the operating conditions of the separation operations, which increases the risks of blocking of the filters with the polymers produced within the said filters.

The dyes used have different natures and often contain heteroatoms of O and N type, and conjugated unsaturations, such as, for example, quinone, methine or azo functional groups, or molecules such as pyrazolone and quinophthalone.

The recycling of coloured or opaque PETs is thus extremely problematic.

Patent EP 0 865 464 describes a process for the recycling by depolymerization of polyesters comprising stages of depolymerization in the presence of a diol, of evaporation of the diol, of dissolution of the mixture in a hot solvent, of filtration and of precipitation of the filtered solution, it being possible for the precipitate to be subsequently used in the preparation of a new polymer. This document describes that the monomers and oligomers can be separated in a thin film evaporator, without, however, specifying under what conditions this evaporator has to be operated. Neither does this patent tackle the problems related to the nature of the treated PET.

Patent JP3715812 describes the production of refined BHET from PET. The depolymerization is followed by a stage of prepurification by cooling, filtration, adsorption and treatment on an ion-exchange resin which is presented as very important, carried out before the evaporation of the glycol and the purification of the BHET. The prepurification makes it possible to prevent the repolymerization of the BHET in the subsequent purification stages. This process operates perfectly as long as the feedstock contains solid impurities which are simple to separate (plastics other than PET, solid residues). On the other hand, passing through a stage of filtration and ion-exchange resin is extremely problematic when the feedstock comprises a large amount of very small solid particles, such as pigments, which is the case when the feedstock treated comprises opaque PET, in particular in sizeable proportions (more than 10% by weight of opaque PET).

Patent EP 0 865 464 describe the recycling by depolymerization of polyesters by a diol, followed by a stage of evaporation of the diol, and then by dilution in a solvent under hot conditions. This dilution under hot conditions makes it possible to separate, by filtration, the impurities with a size of greater than 50 µm. The solution treated is subsequently cooled and the precipitated constituents repolymerized. The filtration stage makes it possible to remove the insoluble impurities. The low proportion of pigments in coloured PET makes possible separation by filtration. However, this technology cannot operate with the amount of pigments present in opaque PET, these pigments rapidly blocking the filter.

Patent FR 2 103 115 deals with the purification of BHET by distillation with a very short residence time, in order to prevent the repolymerization of the BHET, mainly for the purpose of removing the impurities resulting from the reaction of terephthalic acid and ethylene oxide. This document teaches that it is relevant to carry out the separation of the BHET at a relatively high temperature (200-350° C.) in order to minimize the residence time in the distillation. This document does not deal with the presence of the other solid impurities, such as the pigments. In point of fact, at elevated temperature, these pigments will greatly favour the polymerization of the BHET.

SUBJECT-MATTER AND ADVANTAGE OF THE INVENTION

A subject-matter of the invention is a process for the depolymerization of a polyester feedstock comprising opaque PET, the said process comprising at least the following stages:
a) a conditioning stage fed by the said polyester feedstock;
b) a stage of depolymerization by glycolysis fed at least by the effluent from stage a) and by a contribution of diol, carried out at a temperature of between 200 and 400° C., with from 1 to 20 mol of diol per mole of diester in the said polyester feedstock and a residence time of the polyester of between 0.1 and 5 h;
c) a stage of separation of the diol fed at least by the effluent from stage b), carried out at a temperature of between 100 and 250° C., at a lower pressure than that of stage b) and producing a diol effluent and a liquid effluent rich in monomers;
d) a stage of separation of the liquid effluent rich in monomers resulting from stage c) into a heavy impurities effluent and a prepurified monomers effluent carried out at a temperature of less than 250° C. and a pressure of less than 0.001 MPa with a liquid residence time of less than 10 min; and
e) a stage of decolouration of the prepurified monomers effluent, carried out at a temperature of between 100 and 250° C. and at a pressure of between 0.1 and 1.0 MPa in the presence of an adsorbent and producing a purified monomers effluent.

An advantage of the invention is to be able to treat polyesters comprising pigments and dyes, in particular azure, coloured, opaque, indeed even multilayer, PETs.

The process according to the invention, capable of treating opaque PET, makes it possible to remove the pigments and dyes and to return to the monomer by chemical reaction. This monomer is subsequently repolymerized to give a polymer which does not exhibit any difference from a virgin polyester, in particular a virgin PET, thus allowing all the uses of virgin PET.

DETAILED DESCRIPTION OF THE INVENTION

Feedstock

The process according to the invention is fed by a polyester feedstock comprising at least one polyester, that is to say a polymer, the repeat unit of the main chain of which contains an ester functional group, and comprising opaque polyethylene terephthalate (PET). The said polyester feedstock advantageously consists of recycled polyesters.

PET, known as polyethylene terephthalate or poly(ethylene terephthalate), is a polymer obtained by the polycondensation of terephthalic acid (PTA) with ethylene glycol, of chemical formula:

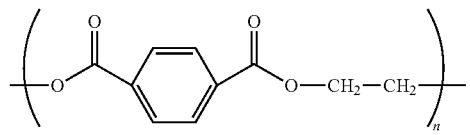

where n represents the number of units in the PET. In the continuation of the text, moles of diester in the said polyester feedstock is understood to mean the number of moles of —[O—CO—($C_6H_4$)—CO—O—$CH_2$—$CH_2$]— unit, which is the diester unit resulting from the reaction of PTA and ethylene glycol, in the PET included in the said polyester feedstock.

Preferably, the said polyester feedstock comprises at least one PET chosen from opaque, dark or multilayer PET and their mixture. More preferably, the said polyester feedstock comprises at least 10% by weight of opaque PET, very preferably at least 15% by weight of opaque PET, the said opaque PET advantageously being recycled opaque PET.

The said feedstock advantageously comprises from 0.1% to 10% by weight of pigment, advantageously from 0.1% to 5% by weight. It advantageously comprises from 0.05% to 1% by weight of dyes, advantageously from 0.05% to 0.2% by weight.

The said polyester feedstock can also comprise up to 2% by weight of impurities, such as metals, other plastics (PP, PEHD, and the like), board or paper, wood or inorganics, and the like. The polyester feedstock can also comprise elements used as polymerization catalyst and as stabilizing agents in the processes for the production of PET, such as antimony, titanium or tin.

The polyesters, advantageously recycled, included in the said feedstock are advantageously washed and ground so as to form a polyester feedstock consisting of flakes, the maximum greatest length of which is less than 10 cm, preferably between 5 and 25 mm.

Conditioning Stage a)

The said process according to the invention comprises a conditioning stage a) fed by the said polyester feedstock.

The said stage a) makes it possible to heat and to pressurize the said polyester feedstock to the operating conditions of the depolymerization stage b).

The feedstock is gradually heated to a temperature greater than its melting point, so as to become liquid. Advantageously, at least 80% by weight of the feedstock is in the liquid form on conclusion of stage a), very advantageously at least 90% by weight and preferably at least 95% by weight on conclusion of stage a). The temperature of the said stage a) is advantageously between 225 and 275° C. This temperature is kept as low as possible in order to minimize the thermal decomposition of the polyester.

Advantageously, the said stage a) comprises a screw conveying section, referred to as extrusion section, fed by the said polyester feedstock.

The residence time in the said extrusion section, defined as the volume of the said section divided by the volume flow rate of feedstock, is advantageously less than 15 min, preferably less than 10 min and preferably less than 2 min.

The said extrusion section is advantageously connected to a vacuum extraction system so as to remove impurities, such as dissolved gases, light organic compounds and/or moisture present in the feedstock. The said extrusion section can also advantageously comprise a filtration system in order to remove solid particles with a size of greater than 40 µm, preferably with a size of between 3 and 40 µm, such as sand particles.

The said polyester feedstock is advantageously brought into contact with at least a fraction of the diol effluent resulting from stage c), advantageously within the said extrusion section. This contacting operation has the effect of initiating the depolymerization reaction before the introduction into the depolymerization stage b). In this case, the term used is reactive extrusion section. The diol effluent resulting from stage c) can advantageously be superheated prior to feeding it in stage a), in order to make it easier to bring the polyester feedstock to temperature. The number of moles of diol resulting from stage c) per mole of diester in the said polyester feedstock is advantageously less than 1.0 and in a preferred way less than 0.5.

The said polyester feedstock can also advantageously be fed as a mixture with a fraction of the heavy impurities effluent resulting from stage d), the said fraction preferably having been purified in a filtration stage.

Depolymerization Stage b)

The process according to the invention comprises a stage of depolymerization by glycolysis fed at least by the effluent from the said stage a) and by a contribution of diol, carried out at a temperature of between 200 and 400° C., preferably between 230 and 350° C., in a preferred way between 250 and 300° C., in the liquid phase, with from 1 to 20 mol of diol per mole of diester in the said polyester feedstock, preferably from 3 to 15 and in a preferred way from 5 to 10 mol per mole, and a residence time in the said stage b) of between 0.1 and 5 h, preferably between 0.5 and 3 h.

The operating pressure of the said stage b) is determined so as to keep the reaction system in the liquid phase. This pressure is at least 0.1 MPa, preferably at least 0.4 MPa. The term "reaction system" is understood to mean all of the constituents and phases present within the said stage b) which result from the feeding of the said stage.

The residence time is defined as the ratio of the volume of liquid of the said reaction section to the sum of the volume flow rate of the polyester feedstock and of the contribution of diol.

The diol is advantageously monoethylene glycol.

The said depolymerization stage b) advantageously comprises one or more reaction sections. Each reaction section can be employed in any type of reactor known to a person skilled in the art which makes it possible to carry out a depolymerization or transesterification reaction, preferably in a reactor stirred by a mechanical stirring system and/or by a recirculation loop and/or by fluidization. The said reactor can comprise a conical bottom which makes it possible to bleed off the impurities.

The glycolysis reaction can be carried out in the presence or absence of a catalyst. When the glycolysis reaction is carried out in the presence of a catalyst, the latter can be homogeneous or heterogeneous and chosen from the esterification catalysts known to a person skilled in the art, such as complexes, oxides and salts of antimony, tin or titanium, alkoxides of metals from Groups (I) and (IV) of the Periodic Table of the Elements, organic peroxides or acidic/basic metal oxides.

A preferred heterogeneous catalyst advantageously comprises at least 50% by weight, with respect to the total weight of the catalyst, preferably at least 70% by weight, advantageously at least 80% by weight, very advantageously at least 90% by weight and more advantageously still at least 95% by weight of a solid solution composed of at least one spinel of formula $Z_xAl_2O_{(3+x)}$ in which x is between 0 (limit excluded) and 1 and Z is chosen from Co, Fe, Mg, Mn, Ti or Zn, and comprising at most 50% by weight of alumina and of oxide of the element Z. The said preferred heterogeneous catalyst advantageously contains at most 10% by weight of dopants chosen from silicon, phosphorus and boron, taken alone or as a mixture. For example, and without limitation, the said solid solution can consist of a mixture of spinel $ZnAl_2O_4$ and of spinel $CoAl_2O_4$, or else consist of a mixture of spinel $ZnAl_2O_4$, of spinel $MgAl_2O_4$ and of spinel $FeAl_2O_4$, or else consist solely of spinel $ZnAl_2O_4$.

The specific arrangement in which the said preferred heterogeneous catalyst is employed has the advantage of an excellent conversion of PET by glycolysis to give BHET. Furthermore, the heterogeneous catalyst of this specific arrangement has as surprising property that of capturing the impurities, in particular the dyes, the additives and the catalytic substances used in the polymerization and present in the PET treated in the process according to the invention, such as antimony, magnesium, manganese, zinc, titanium or phosphorus, which simplifies the subsequent stages of purification of the BHET for the purpose of its reuse in a polymerization process.

Preferably, the said depolymerization stage is carried out without catalyst.

The said depolymerization stage is advantageously carried out in the presence of a solid adsorbing agent in the powder or shaped form, the role of which is to capture at least a part of the coloured impurities, thus relieving the strain on the decolouration stage e). The said solid adsorbing agent is advantageously an activated carbon.

The glycolysis reaction makes it possible to convert the polyester feedstock into monomers and oligomers of esters, advantageously PET to give bis(2-hydroxyethyl) terephthalate (BHET) monomer and BHET oligomers. The conversion of the polyester feedstock in the said depolymerization stage is greater than 50%, preferably greater than 70%, in a preferred way greater than 85%. The molar BHET yield is greater than 50%, preferably greater than 70%, in a preferred way greater than 85%. The molar BHET yield corresponds to the molar flow rate of BHET at the outlet of the said stage b) to the number of moles of diester in the polyester feedstock feeding the said stage b).

An internal recirculation loop is advantageously employed in stage b), that is to say the withdrawing of a fraction of the reaction system, the filtration of this fraction and the reinjection of the said fraction into the said stage b). This internal loop makes it possible to remove the solid impurities possibly present in the reaction liquid.

Stage c) of Separation of the Diol

The process according to the invention comprises a stage of separation of the diol fed at least by the effluent from stage b), carried out at a temperature of between 100 and 250° C., at a lower pressure than that of stage b) and producing a diol effluent and a liquid effluent rich in monomers.

The main role of stage c) is to recover all or part of the unreacted diol.

Stage c) is carried out at a lower pressure than that of stage b) so as to vaporize a fraction of the effluent from stage b) to give a gas effluent and a liquid effluent. The said liquid effluent constitutes the liquid effluent rich in monomers. The gas effluent, composed to more than 50% by weight of diol, preferably more than 70% by weight, in a preferred way more than 90% by weight, constitutes a gaseous diol effluent which is condensed to give the said diol effluent.

Stage c) is advantageously carried out in a succession of gas/liquid separation sections, advantageously from 1 to 5 successive separation sections, very advantageously from 3 to 5 successive separations. The liquid effluent from the preceding section feeds the subsequent section. All of the gas effluents are condensed to form the diol effluent. The liquid effluent resulting from the final gas/liquid separation section constitutes the liquid effluent rich in monomers.

The temperature and the pressure of the subsequent section are lower than those of the preceding section so that the gas effluent exiting from the preceding section can, on condensing, reboil a part of the liquid effluent of the subsequent section. In this configuration, the contribution of heat for recovering the diol is minimized.

Stage c) is carried out so that the temperature of the liquid effluents is kept above the value below which the polyester monomer precipitates and below a high value, depending on the diol/monomer molar ratio, above which the monomer significantly repolymerizes. The temperature in stage c) is between 100 and 250° C., preferably between 110 and 220° C., in a preferred way between 120 and 210° C. The operation in a succession of gas/liquid separations, advantageously in a succession of 1 to 5, preferably of 3 to 5, successive separations, is particularly advantageous as it makes it possible to adjust, in each separation, the temperature of the liquid effluent corresponding to the abovementioned constraints, which is particularly important as a result of the presence of opaque PET in the polyester feedstock, it being possible for the pigments used to opacify the PET to have a catalytic action in the polymerization reaction of PET.

The pressure in stage c) is adjusted in order to make possible the evaporation of the diol at a temperature which minimizes the repolymerization and which makes possible optimum energy integration. It is generally between 0.00001 and 0.2 MPa, preferably between 0.00004 and 0.15 MPa, in a preferred way between 0.00004 and 0.1 MPa.

The separation section(s) are advantageously stirred by any method known to a person skilled in the art.

The diol effluent can contain other compounds, such as dyes, light alcohols, water or diethylene glycol. At least a fraction of the diol effluent is advantageously recycled to stage a) and/or stage b), advantageously as a mixture with a contribution of diol external to the process according to the invention.

All or part of the said diol effluent can be treated in a purification stage prior to the recycling thereof to stages a) and/or b) and/or the use thereof as a mixture in stage d). This purification stage can comprise, non-exhaustively, an adsorption on a solid (for example on activated carbon), in order to remove the dyes, and one or more distillations, in order to separate the impurities, such as diethylene glycol, water and other alcohols.

Stage d) of Separation of the Monomer

The process according to the invention comprises a stage d) of separation of the effluent rich in monomers resulting from stage c) to give a heavy impurities effluent and a prepurified monomers effluent carried out at a temperature of less than 250° C., preferably of less than 230° C. and very preferably of less than 200° C., and a pressure of less than 0.001 MPa, preferably of less than 0.0005 MPa, with a liquid residence time of less than 10 min, preferably of less than 5 min, in a preferred way of less than 1 min.

The objective of this separation stage is to separate the monomer, which is vaporized, from the oligomers and the polyester, which remain liquid and thus capture the heavy impurities, in particular the pigments, unconverted polymer, other polymers possibly present and polymerization catalysts, while minimizing the loss of monomers by repolymerization. A few oligomers can be entrained with the monomer.

The complete removal of the pigments by filtration is particularly difficult due to the very small size of the said pigments. The effluent rich in monomers resulting from stage c) advantageously comprises a total content of cations and anions of more than 50 ppm, very advantageously of more than 100 ppm.

As a result of the possible presence in the polyester feedstock of polymerization catalysts, in particular if this feedstock comprises opaque PET, this operation has to be carried out with very short liquid residence times and at a temperature not exceeding 250° C. It is thus not possible to envisage a separation by simple atmospheric distillation. Some pigments used to opacify PET, such as $TiO_2$, are known to catalyse the polymerization reaction.

The separation stage d) is advantageously carried out in a falling film or thin film evaporation system or by short path falling film or thin film distillation. The very low operating pressure is necessary in order to be able to carry out stage d) at a temperature of less than 250° C., preferably of less than 230° C., while making it possible to evaporate the monomer.

A polymerization inhibitor is advantageously mixed with the liquid effluent rich in monomers before being fed in the said stage d).

A flux is advantageously mixed with the liquid effluent rich in monomers before being fed in the said stage d), so as to facilitate the removal of the heavy impurities, in particular the pigments, at the bottom of the short path distillation or evaporation system. This flux has to have a much greater boiling point than BHET under the operating conditions of stage d). It can, for example, be polyethylene glycol, or PET oligomers.

The said heavy impurities effluent in particular comprises pigments, oligomers and unseparated BHET. A fraction of the said heavy impurities effluent can advantageously be recycled to the conditioning and feeding stage a) and/or to the depolymerization stage b).

The said heavy impurities effluent advantageously undergoes at least one purification stage, preferably a filtration stage, prior to the recycling thereof, so to reduce the amount of pigments and/or other solid impurities. All or part of the said heavy impurities effluent can also advantageously be bled from the process and sent to an incineration system.

A fraction of the diol effluent can advantageously be mixed with the heavy impurities effluent resulting from stage d) so as to reduce the viscosity of the said heavy impurities effluent and to facilitate the transportation thereof to stage a) and/or stage b), and possibly the treatment thereof in an optional filtration stage.

The said prepurified monomer effluent is advantageously sent to a gas/liquid separation section, which separation is carried out in any item of equipment known to a person skilled in the art, at a temperature of between 100 and 250° C., preferably between 110 and 200° C. and in a preferred way between 120 and 180° C., and at a pressure of between 0.00001 and 0.1 MPa, preferably between 0.00001 and 0.01 MPa and in a preferred way between 0.00001 and 0.001

MPa. The said separation section makes it possible to separate a gaseous diol effluent and a prepurified liquid monomer effluent. The said gas/liquid separation makes it possible to further reduce the amount of diol remaining in the prepurified monomer effluent by recovering, in the said gaseous diol effluent, more than 50% by weight, preferably more than 70% by weight and in a preferred way more than 90% by weight of the diol entrained in stage d) with the prepurified monomer effluent. The amount of monomer entrained in the said gaseous diol effluent is preferably less than 1% by weight, preferably less than 0.1% by weight and in a more preferred way less than 0.01% by weight of the amount of monomer present in the prepurified monomer effluent. The said gaseous diol effluent is subsequently advantageously condensed, optionally pretreated in a purification stage and recycled with the diol effluent resulting from stage c) to stage a) and/or stage b) and/or as a mixture in stage d).

Decolouration Stage e)

The process according to the invention comprises a stage of decolouration of the prepurified monomers effluent, carried out at a temperature of between 100 and 250° C., preferably between 110 and 200° C. and in a preferred way between 120 and 180° C., and at a pressure of between 0.1 and 1.0 MPa, preferably between 0.2 and 0.8 MPa and in a preferred way between 0.3 and 0.5 MPa, in the presence of an adsorbent and producing a purified monomers effluent.

The said adsorbent can be any adsorbent known to a person skilled in the art capable of capturing dyes, such as activated carbon or clays, advantageously an activated carbon.

The prepurified monomers effluent is advantageously mixed with a fraction of the diol effluent resulting from stage c) or with a contribution of diol external to the process according to the invention.

The purified monomer effluent advantageously feeds a polymerization stage known to a person skilled in the art for the purpose of producing PET which is not distinguished in any way from virgin PET, advantageously downstream of the feeding with ethylene glycol, with terephthalic acid or with dimethyl terephthalate, depending on the polymerization stage selected. The feeding of the purified monomer effluent in a polymerization stage makes it possible to reduce, by an equivalent flow rate, the feeding with dimethyl terephthalate or with terephthalic acid.

EXAMPLES

Example 1

In Accordance

This example illustrates the use of the process according to the invention with a feedstock comprising 20% by weight of opaque PET 4 kg/h of flakes resulting from a recycled, ground and washed PET feedstock, composed to 20% by weight of opaque PET and comprising 5% by weight of pigment $TiO_2$, and 12.9 kg/h of ethylene glycol (MEG), are brought to a temperature of 250° C. and then injected into a stirred reactor maintained at a pressure of 0.4 MPa. The residence time, defined as the ratio of the liquid volume of the reactor to the sum of the liquid volume flow rates entering the reactor, is set at 5 h. At the outlet of the reactor, the reaction effluent consists of 69.06% by weight of MEG, 27.74% by weight of BHET, 2.96% by weight of BHET dimer and 0.24% by weight of $TiO_2$.

The ethylene glycol present in the reaction effluent is separated by evaporation in a succession of 4 round-bottomed flasks at temperatures ranging from 210° C. to 130° C. and pressures from 0.12 MPa to 0.001 MPa. On conclusion of this evaporation stage, an MEG stream of 11.1 kg/h and a liquid stream rich in BHET of 5.84 kg/h are recovered. The MEG stream is composed virtually exclusively of ethylene glycol and can thus be recycled to the depolymerization reactor. The liquid stream rich in BHET consists of 80.50% by weight of BHET, 8.52% by weight of BHET dimer, 10.3% by weight of MEG and 0.68% by weight of $TiO_2$.

The liquid stream rich in BHET is subsequently injected into a thin film evaporator at a temperature of 220° C. and a pressure of 50 Pa. The residence time in the thin film evaporator is 1 min. A gas effluent with a flow rate of 5.2 kg/h is recovered at the top of the thin film evaporator. It consists of 88.5% by weight of BHET and 11.5% by weight of MEG and is devoid of trace of $TiO_2$. A heavy residue with a flow rate of 0.64 kg/h is recovered at the bottom of the thin film evaporator and consists of 93.75% by weight of BHET oligomers and 6.25% by weight of $TiO_2$.

The gas effluent is condensed at 130° C. to give a prepurified BHET liquid stream. The prepurified BHET liquid stream is compressed up to 0.5 MPa and subsequently feeds a fixed bed of activated carbon having an adsorption capacity equal to 5% of its weight. On conclusion of this stage, a decoloured and depigmented BHET liquid stream is recovered, which stream is reinjected into a polymerization stage known to a person skilled in the art for the purpose of producing virgin PET.

Example 2

In Accordance

This example illustrates the use of the process according to the invention with a 100% opaque PET feedstock.

4 kg/h of flakes resulting from a recycled, ground and washed PET feedstock, consisting 100% of opaque PET, including 5% by weight of pigment $TiO_2$, and 12.9 kg/h of ethylene glycol (MEG), are brought to a temperature of 250° C. and then injected into a stirred reactor maintained at a pressure of 0.4 MPa. The residence time, defined as the ratio of the liquid volume of the reactor to the sum of the liquid volume flow rates entering the reactor, is set at 5 h. At the outlet of the reactor, the reaction effluent consists of 69.82% by weight of MEG, 26.63% by weight of BHET, 2.37% by weight of BHET dimer and 1.18% by weight of $TiO_2$.

The ethylene glycol present in the reaction effluent is separated by evaporation in a succession of 4 round-bottomed flasks at temperatures ranging from 210° C. to 130° C. and pressures from 0.12 MPa to 0.001 MPa. On conclusion of this evaporation stage, an MEG stream of 11.2 kg/h and a liquid stream rich in BHET of 5.7 kg/h are recovered. The MEG stream is composed virtually exclusively of ethylene glycol and can thus be recycled to the depolymerization reactor. The liquid stream rich in BHET is composed of 78.9% by weight of BHET, 7.0% by weight of BHET dimer, 10.5% by weight of MEG and 3.51% by weight of $TiO_2$.

The liquid stream rich in BHET is subsequently injected into a thin film evaporator at a temperature of 220° C. and a pressure of 50 Pa. The residence time in the thin film evaporator is 1 min. A gas effluent with a flow rate of 5.2 kg/h is recovered at the top of the thin film evaporator. It consists of 88% by weight of BHET and 12% by weight of MEG and is devoid of trace of $TiO_2$. A heavy residue with a flow rate of 0.64 kg/h is recovered at the bottom of the thin film evaporator and consists of 75% by weight of BHET oligomers and 25% by weight of $TiO_2$.

The gas effluent is condensed at 130° C. to give a prepurified BHET liquid stream. The prepurified BHET liquid stream is compressed up to 0.5 MPa and subsequently feeds a fixed bed of activated carbon having an adsorption capacity equal to 5% of its weight. On conclusion of this stage, a decoloured and depigmented BHET liquid stream is recovered, which stream is reinjected into a polymerization stage known to a person skilled in the art for the purpose of producing virgin PET.

Example 3

Not in Accordance

This example illustrates the use of a process according to the prior art (JP3715812) with a feedstock comprising opaque PET 4 kg/h of flakes resulting from a recycled, ground and washed PET feedstock, composed to 20% by weight of opaque PET and comprising 5% by weight of pigment $TiO_2$, and 12.9 kg/h of ethylene glycol (MEG), are brought to a temperature of 250° C. and then injected into a stirred reactor maintained at a pressure of 0.4 MPa. The residence time, defined as the ratio of the liquid volume of the reactor to the sum of the liquid volume flow rates entering the reactor, is set at 5 h. At the outlet of the reactor, the reaction effluent consists of 69.06% by weight of MEG, 27.74% by weight of BHET, 2.96% by weight of BHET dimer and 0.24% by weight of $TiO_2$.

The document JP3715812 teaches that it is necessary and important to carry out a prepurification, that is to say a filtration (40-100 microns) stage, followed by a deionization stage, before the use of a short contact time separator, this prepurification making it possible to extract, from the stream, the entities which promote the reactions for the repolymerization and colouration of the BHET.

The depolymerization effluent is pumped and filtered at 100° C. and 0.4 MPa over a cartridge filter with a porosity of 44 microns (325 mesh), then cooled to 50° C. and sent to a fixed bed containing an ion-exchange resin. The pressure is continuously monitored upstream of the filter and downstream of the resin bed. The pressure increases slowly in the first hours of operation and the difference in pressure between the upstream of the filter and the downstream of the resin bed remains less than 2 bar, which makes it possible to keep the resin bed intact. At the end of 12 h of operation, the pressure increases strongly, up to 8 bar, and the unit is halted 30 min later because of blocking and of a loss of structure of the resin bed. The difference in pressure between the upstream of the filter and the downstream of the resin bed is measured at 6 bar before blocking.

The sequences of stages of the prior art employing a prepurification by filtration and adsorption on a resin thus do not make it possible to treat with a feedstock containing opaque PET in an amount of greater than 10% by weight.

The invention claimed is:

1. A process comprising depolymerization of a polyester feedstock comprising opaque PET, the said feedstock comprising from 0.1% to 10% by weight of pigment, the said process comprising at least:
    a) conditioning the polyester feedstock;
    b) depolymerization by glycolysis of the effluent from a) with diol, carried out at a temperature of between 200 and 400° C., with from 1 to 20 mol of diol per mole of diester in the said polyester feedstock and a residence time of the polyester of between 0.1 and 5 h, converting the PET into BHET monomer and BHET oligomers;
    c) separation of the diol from the effluent from b), carried out at a temperature of between 100 and 250° C., at a lower pressure than that of b) and producing a diol effluent and a liquid effluent rich in monomers, carried out in 1 to 5 successive gas/liquid separation sections, the liquid effluent from a preceding section feeding a subsequent section, all of the gas effluents being condensed to form the diol effluent, a liquid effluent resulting from the final gas/liquid separation section comprising the liquid effluent rich in monomers;
    d) separation of the liquid effluent rich in monomers resulting from c) into a heavy impurities effluent and a prepurified monomers effluent carried out at a temperature of less than 250° C. and a pressure of less than 0.001 MPa with a liquid residence time of less than 10 min; and
    e) decoloration of the prepurified monomers effluent, carried out at a temperature of between 100 and 250° C. and at a pressure of between 0.1 and 1.0 MPa in the presence of an adsorbent and producing a purified monomers effluent.

2. The process according to claim 1, in which the said polyester feedstock comprises at least 10% by weight of opaque PET.

3. The process according to claim 1, in which a) is carried out at a temperature of between 225 and 275° C.

4. The process according to claim 1, in which the said stage a) comprises an extrusion section.

5. The process according to claim 1, in which the said polyester feedstock is brought into contact with at least a fraction of the diol effluent resulting from c) in a).

6. The process according to claim 1, in which b) is carried out in the presence of a solid adsorbent.

7. The process according to claim 1, in which b) is carried out in the presence of a heterogeneous catalyst comprising at least 50% by weight, with respect to the total weight of the catalyst, of a solid solution composed of at least one spinel of formula $Z_xAl_2O_{(3+x)}$ in which x is between 0 (limit excluded) and 1 and Z is Co, Fe, Mg, Mn, Ti or Zn, and comprising at most 50% by weight of alumina and of oxide of the element Z.

8. The process according to claim 1, in which a fraction of the diol effluent resulting from c) is recycled to b).

9. The process according to claim 1, in which d) is carried out at a pressure of less than 0.0005 MPa.

10. The process according to claim 1, in which d) is carried out with a liquid residence time of less than 1 min.

11. The process according to claim 1, in which a fraction of the said heavy impurities effluent is recycled to conditioning in a) and/or to the depolymerization b).

12. The process according to claim 11, in which a fraction of the diol effluent resulting from c) is mixed with the heavy impurities effluent resulting from d).

13. The process according to claim 1, in which the prepurified monomer effluent resulting from d) is sent to a gas/liquid separation section, which separation is carried out at a temperature of between 100 and 250° C. and at a pressure of between 0.00001 and 0.1 MPa.

14. The process according to claim 1, in which the purified monomer effluent feeds a polymerization producing PET.

15. The process according to claim 1, wherein the feedstock comprises 0.25 to 10% by weight of pigment.

* * * * *